(12) United States Patent
Gyarfas et al.

(10) Patent No.: US 10,288,599 B2
(45) Date of Patent: *May 14, 2019

(54) SYSTEMS AND DEVICES FOR MOLECULE SENSING AND METHOD OF MANUFACTURING THEREOF

(71) Applicant: ARIZONA BOARD OF REGENTS on behalf of ARIZONA STATE UNIVERSITY, Scottsdale, AZ (US)

(72) Inventors: Brett Gyarfas, Chandler, AZ (US); Stuart Lindsay, Phoenix, AZ (US); Pei Pang, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/002,828

(22) Filed: Jan. 21, 2016

(65) Prior Publication Data

US 2016/0258925 A1    Sep. 8, 2016

Related U.S. Application Data

(63) Continuation of application No. 14/051,142, filed on Oct. 10, 2013, now Pat. No. 9,274,430.

(Continued)

(51) Int. Cl.
*G01N 33/487* (2006.01)
*G03F 7/20* (2006.01)
(Continued)

(52) U.S. Cl.
CPC ..... *G01N 33/48721* (2013.01); *C12Q 1/6869* (2013.01); *G01N 27/44791* (2013.01); *G03F 7/20* (2013.01)

(58) Field of Classification Search
CPC ....... G01N 33/48721; G01N 27/44791; C12Q 1/6869

See application file for complete search history.

(56) References Cited

U.S. PATENT DOCUMENTS 3,619,206 A    11/1971   Irons et al.
4,804,707 A    2/1989    Okamoto et al.
(Continued)

FOREIGN PATENT DOCUMENTS

EP    1261863 B1    2/2005
WO    WO 1992/001476 A1    2/1992
(Continued)

OTHER PUBLICATIONS

Aksimentiev, A et al. "Microscopic Kinetics of DNA Translocation through Synthetic Nanopores." Biophys. J. (2004), 87.3: 2086-2097.

(Continued)

*Primary Examiner* — Melanie Brown
(74) *Attorney, Agent, or Firm* — Schwabe, Williamson & Wyatt, P.C.

(57) ABSTRACT

Embodiments of the disclosure are directed to a device for molecule sensing. In some embodiments, the device includes a first electrode separated from a second electrode by a dielectric layer. The first electrode comprises a large area electrode and the second electrode comprises a small area electrode. At least one opening (e.g., trench) cut or otherwise created into the dielectric layer exposes a tunnel junction therebetween whereby target molecules in solution can bind across the tunnel junction.

11 Claims, 12 Drawing Sheets

Cross Section

Related U.S. Application Data

(60) Provisional application No. 61/711,981, filed on Oct. 10, 2012.

(51) Int. Cl.
  *C12Q 1/6869* (2018.01)
  *G01N 27/447* (2006.01)

(56) References Cited

U.S. PATENT DOCUMENTS

| | | |
|---|---|---|
| 5,066,716 A | 11/1991 | Robey et al. |
| 5,879,436 A | 3/1999 | Kramer et al. |
| 6,215,798 B1 | 4/2001 | Carneheim et al. |
| 6,537,755 B1 | 3/2003 | Drmanac |
| 6,627,067 B1 | 9/2003 | Branton et al. |
| 6,821,730 B2 | 11/2004 | Hannah |
| 6,824,974 B2 | 11/2004 | Pisharody et al. |
| 6,905,586 B2 | 6/2005 | Lee et al. |
| 7,001,792 B2 | 2/2006 | Sauer et al. |
| 7,033,476 B2 | 4/2006 | Lee et al. |
| 7,282,130 B2 | 10/2007 | Flory |
| 7,638,034 B2 | 12/2009 | Sansinena et al. |
| 7,700,306 B2 | 4/2010 | Thompson et al. |
| 8,003,319 B2 | 8/2011 | Polonsky et al. |
| 8,278,055 B2 | 10/2012 | Su et al. |
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,952,198 B2 | 4/2018 | Lindsay et al. |
| 9,981,997 B2 | 5/2018 | Zhang et al. |
| 2002/0033345 A1 | 3/2002 | Meade |
| 2002/0117659 A1 | 8/2002 | Lieber et al. |
| 2003/0089605 A1 | 5/2003 | Timperman |
| 2003/0099951 A1 | 5/2003 | Akeson et al. |
| 2003/0148289 A1 | 8/2003 | Sundararajan et al. |
| 2003/0203394 A1 | 10/2003 | Eichen et al. |
| 2003/0215376 A1 | 11/2003 | Chopra |
| 2004/0128081 A1 | 7/2004 | Rabitz et al. |
| 2004/0144658 A1 | 7/2004 | Flory |
| 2004/0262636 A1 | 12/2004 | Yang et al. |
| 2005/0032053 A1 | 2/2005 | Sampson |
| 2005/0095599 A1 | 5/2005 | Pittaro et al. |
| 2005/0136408 A1 | 6/2005 | Tom-Moy et al. |
| 2005/0202444 A1 | 9/2005 | Zhu |
| 2005/0217990 A1 | 10/2005 | Sibbett et al. |
| 2006/0073489 A1 | 4/2006 | Li et al. |
| 2006/0194228 A1 | 8/2006 | Rakitin et al. |
| 2006/0211016 A1 | 9/2006 | Kayyem et al. |
| 2006/0263255 A1 | 11/2006 | Han et al. |
| 2007/0009379 A1 | 1/2007 | Bau et al. |
| 2007/0138132 A1 | 6/2007 | Barth |
| 2007/0154890 A1 | 7/2007 | Isobe |
| 2007/0292855 A1 | 12/2007 | Dubin et al. |
| 2008/0050752 A1 | 2/2008 | Sun et al. |
| 2008/0121534 A1 | 5/2008 | White et al. |
| 2008/0171316 A1 | 7/2008 | Golovchenko et al. |
| 2009/0198117 A1 | 8/2009 | Cooper et al. |
| 2009/0298072 A1 | 12/2009 | Ju et al. |
| 2009/0308741 A1 | 12/2009 | Frey et al. |
| 2009/0309614 A1 | 12/2009 | Goodman et al. |
| 2009/0326238 A1 | 12/2009 | Burn et al. |
| 2010/0084276 A1 | 4/2010 | Lindsay et al. |
| 2010/0145626 A1 | 6/2010 | Ecker et al. |
| 2010/0267158 A1 | 10/2010 | Chou et al. |
| 2010/0292101 A1 | 11/2010 | So |
| 2010/0294659 A1 | 11/2010 | Green |
| 2010/0310421 A1 | 12/2010 | Oliver et al. |
| 2011/0065164 A1 | 3/2011 | Santoyo Gonzalez et al. |
| 2011/0070735 A1 | 3/2011 | Shi |
| 2011/0120868 A1 | 5/2011 | Lindsay et al. |
| 2011/0124118 A1 | 5/2011 | Park et al. |
| 2011/0168562 A1 | 7/2011 | Nuckolls et al. |
| 2011/0285409 A1 | 11/2011 | Maleki et al. |
| 2012/0052258 A1 | 3/2012 | Op De Beeck et al. |
| 2012/0097539 A1 | 4/2012 | Qian et al. |
| 2012/0122715 A1 | 5/2012 | Gao et al. |
| 2012/0288935 A1 | 11/2012 | Mirkin et al. |
| 2012/0288948 A1 | 11/2012 | Lindsay et al. |
| 2012/0329741 A1 | 12/2012 | Oyelere et al. |
| 2012/0330001 A1 | 12/2012 | Darzins et al. |
| 2013/0186757 A1 | 7/2013 | Reinhart et al. |
| 2013/0123379 A1 | 8/2013 | Nivala et al. |
| 2013/0302901 A1 | 11/2013 | Lindsay et al. |
| 2013/0316912 A1 | 11/2013 | Bjornson et al. |
| 2014/0005509 A1 | 1/2014 | Bhavaraju et al. |
| 2015/0010935 A1 | 1/2015 | Lindsay et al. |
| 2015/0142327 A1 | 5/2015 | Ashcroft et al. |
| 2015/0144506 A1 | 5/2015 | Lindsay et al. |
| 2016/0025702 A1 | 1/2016 | Lindsay et al. |
| 2016/0108002 A1 | 4/2016 | Zhang et al. |
| 2016/0177383 A1 | 6/2016 | Ashcroft et al. |
| 2016/0194698 A1 | 7/2016 | Lindsay |
| 2017/0003245 A1 | 1/2017 | Lindsay et al. |
| 2017/0016852 A1 | 1/2017 | Lindsay et al. |
| 2017/0067902 A1 | 3/2017 | Zhang et al. |
| 2017/0137389 A1 | 5/2017 | Zhang et al. |
| 2017/0204066 A1 | 7/2017 | Lindsay et al. |
| 2017/0343558 A1 | 11/2017 | Lindsay et al. |

FOREIGN PATENT DOCUMENTS

| | | |
|---|---|---|
| WO | WO 1999/057550 A1 | 11/1999 |
| WO | WO 01/92890 A1 | 12/2001 |
| WO | WO 2003/031464 A2 | 4/2003 |
| WO | WO 2007/084163 A2 | 7/2007 |
| WO | WO 2008/071982 A2 | 6/2008 |
| WO | WO 2008/124706 A2 | 10/2008 |
| WO | WO 2008/124706 A9 | 10/2008 |
| WO | WO 2009/117517 A2 | 9/2009 |
| WO | WO 2009/117522 A2 | 9/2009 |
| WO | WO 2010/042514 A1 | 4/2010 |
| WO | WO 2011/067964 A1 | 6/2011 |
| WO | WO 2011/097171 A1 | 8/2011 |
| WO | WO 2012/155007 A1 | 11/2012 |
| WO | WO 2013/116509 A1 | 8/2013 |
| WO | WO 2013/123379 A2 | 8/2013 |
| WO | WO 2013/148344 A1 | 10/2013 |
| WO | WO 2013/180819 A1 | 12/2013 |

OTHER PUBLICATIONS

Ashkenasy et al. "Recognizing a Single Base in an Individual DNA Strand: A Step Toward DNA Sequencing in Nanopores." Angew. Chem. Int. Ed. Engl. (2005), 44.9: 1401-1404.

Astier et al. "Toward Single Molecule DNA Sequencing: Direct Identification of Ribonucleoside and Deoxyribonucleoside 5'-Monophosphates by Using an Engineered Protein Nanopore Equipped with a Molecular Adapter." J. Am. Chem. Soc. 128 (2006): 1705-1710.

Bacri, L. et al. "Discrimination of neutral ollgosaccharides through a nanopore." Biochemical and Biophysical Research Communications (2011), 412(4): 561-564.

Boersma et al. "Real-Time Stochastic Detection of Multiple Neurotransmitters with a Protein Nanopore." ACSnano (2012), 6(6): 5304-5308.

Boersma et al. "Continuous Stochastic Detection of Amino Acid Enantiomers with a Protein Nanopore." Angew. Chem. Int. Ed. (2012), 51: 9606-9609.

Branton et al. "The Potential and Challenges of Nanopore Sequencing." Nat. Biotechnol. (2008), 26.10: 1146-1153.

Bustamante, C. et al. Grabbing the cat by the tail: Manipulating molecules one by one., Nature Reviews Molecular Cell Biology (2000), 1: 130-136.

Cannon, Joe et al. "High-Throughput Middle-Down Analysis Using an Orbitrap." Journal of Proteome Research, 2010, 9(8), pp. 3886-3890.

(56) References Cited

OTHER PUBLICATIONS

Chang, H. et al. "Fabrication and characterization of solid state nanopores using field emission scanning electron beam." App. Phys. Lett. (2006), 88: 103109-103109-3.
Chang, H. et al., Towards Integrated Micro-machined silicon-based nanopores for characterization of DNA. In Proc. of Hilton Head Conf. 2004. Hilton Head, SC.
Chang, S. et al. "Chemical Recognition and Binding Kinetics in a Functionalized Tunnel Junction." Nanotechnology (2012), 23(23): 235101.
Chang, S. et al. "Gap Distance and Interactions in a Molecular Tunnel Junction." Journal of the American Chemical Society (2011), 133: 14267-14269. dx.doi.org/10.1021/ja2067737.
Chang, S. et al., Electronic Signatures of all Four DNA Nucleosides in a Tunneling Gap, Nano Letters, No. 10, No. 3, Feb. 8, 2010, pp. 1070-1075.
Chang et al., Tunneling readout of hydrogen-bonding based recognition, Nature Nanotechnology, May 2009, 4(5):297-301.
Chen et al. "Probing single DNA molecule transport using fabricated nanopores." Nano Lett. (2004), 4: 2293-2298.
Chen, P. et al. "Atomic layer deposition to fine-tune the surface properties and diameters of fabricated nanopores." Nano Lett. (2004), 4: 1333.
Chen et al. "Subfemtomole level protein sequencing by Edman degradation carried out in a microfluidic chip." Chem. Commun. (2007), 24: 2488-2490.
Cui, X.D. et al. "Reproducible Measurement of Single-Molecule Conductivity," Science, Oct. 19, 2001, vol. 294, Issue 5542, pp. 571-574.
Cui, X.D. et al. "Changes in the Electronic Properties of a Molecule When It Is Wired into a Circuit", J. Phys. Chem. B, 2002, 106 (34), pp. 8609-8614. Pub. Date (Web): Aug. 2, 2002.
Clarke et al. "Continuous base identification for single-molecule nanopore DNA sequencing." Nature Nanotechnology (2009), 4: 265-270.
Deamer, D.W., et al. "Characterization of nucleic acids by nanopore analysis." Ace. Chem. Res. (2002), 35: 817-825.
Examination Report, dated Nov. 13, 2014, for EP Application No. 11740234.7.
Examination Report, dated Jul. 8, 2014, for EP Application No. 11740234.7.
Feldman et al. "Molecular Electronic Devices Based on Single-Walled Carbon Nanotube Electrodes" Acc. Chem. Res. 2008, 41 (12), pp. 1731-1741. Pub. Date (Web): Sep. 18, 2008.
Fischbein, Michael D. et al. Sub-10 nm Device Fabrication in a Transmission Electron Microscope, Nano Lett, 2007, 7(5), pp. 1329-1337. Pub. Date (Web): Apr. 17, 2007.
Fologea, D., et al. "Detecting single stranded DNA with a solid state nanopore." Nano Lett. (2005), 5(10): 1905-1909.
Fologea, D., et al. "Slowing DNA translocation in a solid-state nanopore", Nano Lett. (2005) 5(9): 1734-1737.
Gao et al. "A Simple Method of Creating a Nanopore-Terminated Probe for Single-Molecule Enantiomer Discrimination." Anal. Chem. (2009), 81: 80-86.
Gracheva, M.E. et al. "Simulation of the electric response of DNA translocation through a semiconductor nanopore capacitor." Nanotechnology (2006), 17: 622-633.
He et al. "Functionalized Nanopore-Embedded Electrodes for Rapid DNA Sequencing." The Journal of Physical Chemistry Letters (2008), 112: 3456-3459 (published on Web Feb. 14, 2008).
He, J. et al. "Identification of DNA Basepairing via Tunnel-Current Decay." Nano Letters (2007), 7(12): 3854-3858.
He, J. et al., "A hydrogen-bonded electron-tunneling circuit reads the base composition of unmodified DNA." 2009 Nanotechnology 20 075102, published Jan. 23, 2009.
Heng, J.B. et al. "The detection of DNA using a silicon nanopore. in Electron Devices Meeting, 2003." IEDM '03 Technical Digest. 2003: IEEE International.
Heng, J.B. et al. "Sizing DNA using a nanometer-diameter pore." Biophys J. (2005), 87: 2905-2911.

Heng, J.B. et al., "The electromechanics of DNA in a ysnthetic nanopore." Biophysical Journal (2006), 90(3): 1098-1106.
Huang, et al. "Identifying single bases in a DNA oligomer with electron tunnelling" Nature Nanotechnology vol. 5, No. 12, Nov. 14, 2010, pp. 868-873.
International Search Report and Written Opinion, dated Oct. 1, 2008 for International Application No. PCT/US2008/059602.
International Preliminary Report on Patentability, dated Oct. 6, 2009 for International Application No. PCT/US2008/059602.
International Search Report and Written Opinion, dated Jan. 25, 2010 for International Application No. PCT/US2009/037570.
International Preliminary Report on Patentability, dated Sep. 30, 2010 for International Application No. PCT/US2009/037570.
International Search Report and Written Opinion, dated Nov. 2, 2009, for International Application No. PCT/US2009/037563.
International Preliminary Report on Patentability, dated Sep. 30, 2010 for International Application No. PCT/US2009/037563.
International Search Report and Written Opinion, dated Dec. 17, 2009 for International Application No. PCT/US2009/059693.
International Preliminary Report on Patentability, dated Apr. 21, 2011 for International Application No. PCT/US2009/059693.
International Search Report and Written Opinion, dated Apr. 8, 2011 for International Application No. PCT/US2011/023185.
International Preliminary Report on Patentability, dated Aug. 16, 2012, for International Application No. PCT/US2011/023185.
International Search Report and Written Opinion, dated Jun. 12, 2013, for PCT/US2013/032240.
International Preliminary Report on Patentability, dated Oct. 16, 2014, for PCT/US2013/032240.
International Search Report and Written Opinion, dated May 31, 2013, for PCT/US2013/032113.
International Preliminary Report on Patentability, dated Dec. 11, 2014, for PCT/US2013/032113.
International Search Report and Written Opinion, dated Apr. 15, 2013 for PCT/US2013/024130, filed Jan. 31, 3013.
International Preliminary Report on Patentability, dated Aug. 14, 2014, for PCT/US2013/024130, filed Jan. 31, 3013.
International Search Report and Written Opinion, dated May 30, 2013, for International Application No. PCT/US2013/032346.
International Preliminary Report on Patentability, dated Oct. 9, 2014, for International Application No. PCT/US2013/032346.
International Search Report and Written Opinion, dated Mar. 11, 2014, for PCT/US2013/064337.
International Preliminary Report on Patentability, dated Apr. 23, 2015, for PCT/US2013/064337.
International Search Report and Written Opinion, dated Aug. 22, 2014, for PCT/US2014/024630.
International Preliminary Report on Patentability, dated Sep. 24, 2015 for PCT/US2014/024630.
International Search Report and Written Opinion, dated Aug. 1, 2014, for PCT/US2014/020789.
International Preliminary Report on Patentability, dated Sep. 8, 2015, for International Application No. PCT/US2014/020789.
International Search Report and Written Opinion, dated Dec. 9, 2014, for International Application No. PCT/US2014/039407.
International Preliminary Report on Patentability, dated Dec. 3, 2015, for International Application No. PCT/US2014/039407.
International Search Report and Written Opinion, dated Oct. 15, 2014, for International Application No. PCT/US2014/040323.
International Preliminary Report on Patentability, dated Dec. 10, 2015, for International Application No. PCT/US2014/040323.
International Search Report and Written Opinion, dated Mar. 10, 2015, for International Application No. PCT/US2014/062589.
International Preliminary Report on Patentability, dated May 12, 2016, for International Application No. PCT/US2014/062589.
International Search Report and Written Opinion, dated May 29, 2015, for International Application No. PCT/US2015/017519.
International Preliminary Report on Patentability, dated Sep. 9, 2016, for International Application No. PCT/US2015/017519.
International Search Report and Written Opinion, dated May 20, 2015, for International Application No. PCT/US2015/018062.

(56) References Cited

OTHER PUBLICATIONS

Ivanov, Aleksandar P. et al. "DNA Tunneling Detector Embedded in a Nanopore", Nano Letters, vol. 11, No. 1, Jan. 12, 2011, pp. 279-285.
International Preliminary Report on Patentability, dated Sep. 9, 2016, for International Application No. PCT/US2015/018062.
Javey, A. et al. Ballistic Carbon Nanotube Field-Effect Transistors. Nature. Aug. 7, 2003, vol. 424, pp. 654-657.
Kasianowicz et al. "Simultaneous multianalyte detection with a nanometer-scale pore." Anal. Chem. (2001), 73: 2268-2272.
Kim, M.J. et al. "Rapid Fabrication of Uniformly Sized Nanopores and Nanopore Arrays for Parallel DNA Analysis." Advanced Materials (2006), 18: 3149-3153.
Lee et al. GC base sequence recognition by oligo (imidazolecarboxamide) and C-terminus-modified analogues of distamycin deduced from circular dichroism, proton nuclear magnetic resonance, and methidiumpropylethylenediaminetetraacetate-iron(II) footprinting studies. In: Biochemistry, Apr. 27, 1993, vol. 32, No. 16, pp. 4237-4245.
Lee and Sankey et al. "Insights into electron tunneling across hydrogen-bonded base pairs in complete molecular circuits for single-stranded DNA sequencing." Journal of Physics: Condensed Matter (2009), 21(3): 35110.
Lee and Sankey. "Theory of Tunneling Across Hydrogen-Bonded Base Pairs for DNA Recognition and Sequencing." Phys. Rev. E. (2009), 79.5: 051911.
Liang et al. "Synthesis, Physicochemical Properties, and Hydrogen Bonding of 4(5)-Substituted-1H-imidazole-2-carboxamide, A Potential Universal Reader for DNA Sequencing by Recognition Tunneling." Chemistry—A European Journal (2012), 18(19): 5998-6007.
Lindsay, S.M. Single Molecule Electronics and Tunneling in Molecules, Jap. J. Appl. Phys. (2002), 41: 4867-4870.
Lindsay, S.M. "Single Molecule Electronics." Interface (2004), 3: 26-30.
Lindsay, S.M. "Molecular wires and devices: Advances and issues." Faraday Discussions (2006), 131: 403-409.
Lindsay and Ratner, "Molecular Transport Junctions: Clearing Mists." Advanced Materials (2007), 19: 23-31.
Lindsay, S. et al., Recognition Tunneling, Nanotechnology, Jul. 2, 2010; 21(26): 262001-262013.
Lu, J. et al. "Click Chemistry Functionalized Polymeric Nanoparticles Target Corneal Epithelial Cells through RGD-Cell Surface Receptors", Bioconjugate Chem. 2009, 20(1), pp. 87-94, Publication Date (Web): Dec. 18, 2008.
Liu, H. et al. "Translocation of Single-Stranded DNA Through Single-Walled Carbon Nanotubes." Science Jan. 1, 2010, vol. 327, Issue 5961, pp. 64-67.
Liu, Y. et al. "Descreening of Field Effect in Electrically Gated Nanopores", Applied Phys. Lett. 97, 143109 (2010). Published online Oct. 5, 2010.
Lyubchenko, Yuri et al. Chapter 21: "Atomic Force Microscopy Imaging and Probing of DNA, Proteins, and Protein-DNA Complexes: Silatrane Surface Chemistry" Tom Moss and Benoît Leblanc (eds.), DNA-Protein Interactions, vol. 543 Methods in Molecular Biology, pp. 337-351, Mar. 16, 2009.
Meller et al. "Rapid Nanopore Discrimination Between Single Polynucleotide Molecules." PNAS (2000), 97.3: 1079-1084.
Meller et al. "Voltage-Driven DNA Translocations Through a Nanopore." Phys. Rev. Lett. (2001), 86.15: 3435-3438.
Meller et al. "Single molecule measurements of DNA transport through a nanopore." Electrophoresis (2002), 23: 2583-2591.
Mirkin, C.A. et al., Annu. Rev. Phys. Chem. (1992), 43: 7389-7396.
Mohammad, M. et al. "Controlling a Single Protein in a Nanopore through Electrostatic Traps", published (web) Mar. 6, 2008, Journal of the American Chemical Society 2008, vol. 130, No. 12, pp. 4081-4088.
Muller, C.J., et al. , , Experimental observation of the transition from weak link to tunnel juntion, Physica C, 1992. 191: 485-504.

Muenier, V. et al. "Enhancement of the Transverse Conductance in DNA Nucleotides" J. Chem. Phys. 128, 041103 (2008), published online Jan. 29, 2008.
Muthukumar, Theory of sequence effects on DNA translocation through proteins and nanopores, Electrophoresis, 2003. 23: 1417-1420. Published May 23, 2002.
Muthukumar et al. "Simulation of Polymer Translocation Through Protein Channels" PNAS, vol. 103, No. 14 (2006), pp. 5273-5278.
Muthukumar, M., Mechanism of DNA transport through pores, Annual Review of Biophysics and Biomolecular Structure, vol. 36, 2007, pp. 435-450.
Myeong, H. Lee et al. "Insights into electron tunneling across hydrogen-bonded base pairs in complete molecular circuits for single-stranded DNA sequencing", Journal of Physics: Condensed Matter, Institute of Physics Publishing, Bristol, GB, vol. 21, No. 3, Jan. 21, 2009, p. 35110.
Nakane et al. "A nanosensor for transmembrane capture and Identification of single nucleic acid molecules." Biophys J. (2004), 87: 615-621.
Nilsson, J. et al. "Localized Functionalization of Single Nanopores", Adv. Mater. 2006, 18, pp. 427-431. doi:10.1002/adma.200501991.
Nivala, J. et al., Unfoldase-mediated protein translocation through an alpha-hemolysin nanopore, published online Feb. 3, 2013, Nature Biotechnology 31, pp. 247-250 (2013).
Nishino, T. et al. "Carbon Nanotube Scanning Tunneling Microscopy Tips for Chemically Selective Imaging", Analytical Chemistry, American Chemical Society, US, vol. 74, No. 16, Aug. 15, 2002, pp. 4275-4278.
Notice of Reasons for Rejection, dated Jan. 19, 2015, for JP Application No. 2012-551372.
Office Action, dated Dec. 19, 2014 for CN Application No. 201180004174.X.
Office Action and Search Report, dated Feb. 24, 2014 for CN Application No. 201180004174.X.
Oshiro, T. et al. "Complementary base-pair-facilitated electron tunneling for electrically pinpointing complementary nucleobases" In: Proc. Nat. Acad. Sci. (USA) Jan. 3, 2006 vol. 103 No. 1 p. 10-14, especially abstract, p. 11 Fig 1. p. 14 right col. para 1.
Peng et al. "Nanopore-based DNA sequencing and DNA motion control." Nanopores: Sensing and Fundamental Biological Interactions (2011), 11: 255-286.
Peng et al. Slowing down DNA translocation using magnetic and optical tweezers. In: American Physical Society, APS March Meeting, Mar. 13-17, 2006, abstract #N26.010. Available online at «URL: http://meetings.aps.org/Meeting/MAR06/Event/42679».
Porath et al. Direct measurement of electrical transport through DNA molecules. In: Nature Feb. 10, 2000 vol. 403 p. 635-638.
Pressly et al. "Rapid Synthesis of Block and Cyclic Copolymers via Click Chemistry in the Presence of Copper Nanoparticles" J Polym Sci A Polym Chem. Feb. 2011; 49(3): 814-819.
Schug, K.A. et al. Noncovalent Binding between Guanidinium and Anionic Groups: Focus on Biological- and Synthetic-Based Arginine/Guanidinium Interactions with Phosph[on]ate and Sulf[on]ate Residues. In: Chemical Reviews, 2005, vol. 105, No. 1 p. 67-113.
Senapati, Subhadip et al. "Application of Catalyst-free Click Reactions in Attaching Affinity Molecules to Tips of Atomic Force Microscopy for Detection of Protein Biomarkers" Langmuir, 2013, 29(47), pp. 14622-14630, Publication Date (Web): Nov. 3, 2013.
Shimmin et al. Polymer Size and Concentration Effects on the Size of Gold Nanoparticles Capped by Polymeric Thiols. In: Langmuir Jun. 22, 2004 vol. 20 No. 13 p. 5613-5620.
Storm, A. et al. "Fabrication of solid-state nanopores with single-nanometre precision." Nature Mat. (2003), 2: 537-540.
Storm, A. et al. "Translocation of double-strand DNA through a silicon oxide nanopore." Phys. Rev. E (2005), 71: 051903.
Storm, A. et al. "Fast DNA translocation through a solid-state nanopore." Nano Lett. (2005) 5: 1193.
Strobel, S.A. et al. "The 2,6-Diaminopurine Riboside5-Methylisocytidine Wobble Base Pair: An Isoenergetic Substitution for the Study of GU Pairs in RNA." Biochemistry (1994), 33(46): 13824-13835.
Extended European Search Report and Search Opinion, dated Nov. 25, 2013, for EP Application No. 11740234.7.

(56) References Cited

OTHER PUBLICATIONS

Tsutsui, M. et al., Single-molecule identification via electric current noise, published Dec 14, 2010, Nature Communications, 1:138, DOI: 10.1038.

Tsutsui, M. et al., Single-molecule sensing electrode embedded in-plane nanopore, Jul. 28, 2011, Scientific Reports, 1:46, DOI: 10.1038.

Venkatesan et al. "Nanopore sensors for nucleic acid analysis." Nature Nanotechnology (2011), 6: 615-624.

Venkataraman, L. et al, Single-Molecule Circuits with Well-Defined Molecular Conductance, Nano Lett., 2006. 6: 458-462.

Vlassarev, DM. DNA Characterization with Solid-State Nanopores and Combined Carbon Nanotube across Solid-State Nanopore Sensors. Harvard University, Department of Physics. May 2012, p. 90.

Walti et al., Direct Selective Functionalization of Nanometer-Separated Gold Electrodes with DNA Oligonucleotides. In: Langmuir Feb. 2003 vol. 19 No. 4 p. 981-984.

Zwolak et al. "Colloquium: Physical Approaches to DNA Sequencing and Detection." Rev. Mod. Physics. (2008), 80.1: 141-165.

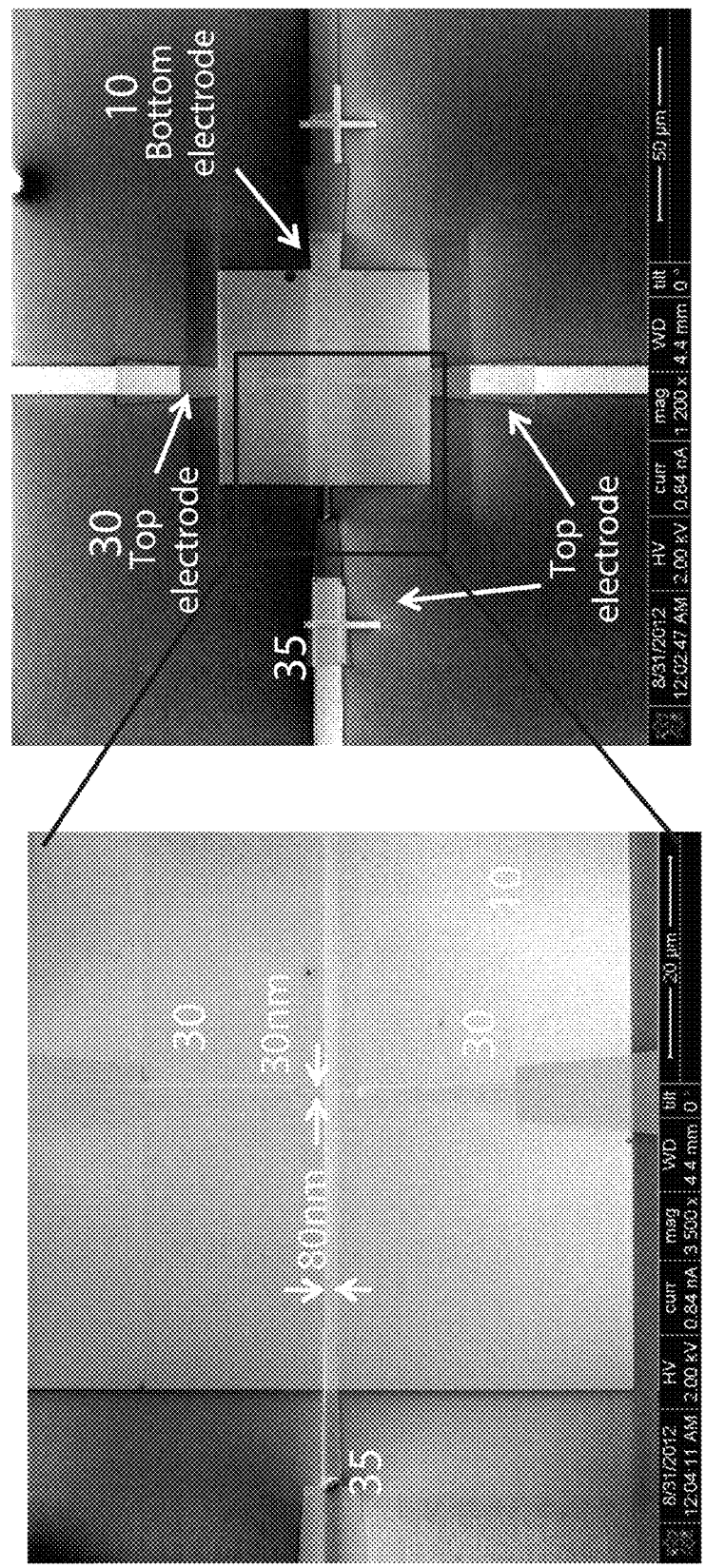

SYSTEMS AND DEVICES FOR MOLECULE SENSING AND METHOD OF MANUFACTURING THEREOF

RELATED APPLICATIONS

The present application is a continuation of U.S. application Ser. No. 14/051,142, filed Oct. 10, 2013, which claims the benefit under 35 USC § 119(e) of U.S. provisional patent application No. 61/711,981, filed Oct. 10, 2012, the entire disclosures of which are herein incorporated by reference.

STATEMENT REGARDING FEDERALLY SPONSORED RESEARCH AND DEVELOPMENT

This invention was made with government support under grant number HG006323 awarded by the National Institute of Health. The government has certain rights in this invention.

FIELD OF THE DISCLOSURE

Embodiments of the present disclosure relate generally to systems, methods and devices for molecule sensing, and more particularly to systems, methods and devices for detecting target molecules, and in some embodiments, single molecule detection. Moreover, other embodiments are directed to methods of manufacture of such systems and devices.

BACKGROUND OF THE DISCLOSURE

In a series of earlier disclosures: WO2009/117522A2, WO2010/042514A1, WO2009/117517, WO2008/124706A2, US2010/0084276A1, and US2012/0288948, each of which is incorporated herein by reference in its entirety, a system is shown where nucleic acid bases are read using the electron tunneling current signals generated as nucleobases pass through a tunnel gap functionalized with adaptor molecules. See also Huang et al.[1] This method is referred to as "Recognition Tunneling".[2]

U.S. non-provisional patent application Ser. No. 13/838,727, filed Mar. 15, 2013, is understood to disclose a readout device constructed from a planar sandwich of a Pd electrode, a layer of dielectric and a top Pd electrode, where a nano sized opening (or nanopore) is drilled by means of an electron beam. However, drilling through a sandwich of materials sometimes presents challenges. For example, sometimes such drilling may damaging the Pd electrodes, which could lead to electrical shorting.

SUMMARY OF THE EMBODIMENTS

Accordingly, it is an object of some of the embodiments of the present disclosure to provide a target molecule recognition tunneling device (e.g., single molecule detection) that, during manufacturing, damage caused by drilling a nano-sized opening (i.e., nanopore) through metal electrodes, is minimized (in some embodiments, such manufacturing eliminates the nano-sized opening altogether). It is another object of some of the embodiments of the present disclosure to provide a device that can be manufactured without one and/or another critical alignment steps for various components and processing, and therefore, easier and, in some embodiments, more economical to mass produce.

It is still another object of some of the embodiments of the present disclosure to cut, etch or otherwise create an opening to and/or through metal electrodes in a tunnel gap in a manner that minimize damage to the tunnel gap.

In some embodiments, a method for manufacturing a device for detecting one or more target molecules is provided and may comprise one or more (and in some embodiments several, and in some embodiments, all of the following steps: depositing a first bottom electrode onto a solid supporting layer wherein the first electrode including a first area, depositing a dielectric layer over the first electrode, depositing a second top electrode over the dielectric layer, wherein the second electrode includes a second area which is substantially less than the first area, and cutting, etching or otherwise creating at least one trench through at least the second electrode and the dielectric layer, such that the bottom of the trench exposes the first electrode and exposes a tunnel junction between the electrodes.

Some embodiments may comprise, and/or otherwise include (e.g., with respect to the above noted embodiments, or other embodiments disclosed herein) one and/or another of the following features and/or steps:

depositing at least one adhesion layer arranged beneath at least one of the first and second electrodes;
the dielectric layer is deposited such that it covers substantially all of the first electrode save for a contact area for the first electrode, the contact area configured for connection to a contact pad at the edge of the device;
depositing $Al_2O_3$ on the contact area;
functionalizing first molecules for forming a non-covalent bond with the one or more target molecules on the electrodes;
depositing a passivating layer between about 20 nm and about 500 nm covering a substantial portion of the surface of at least one of the electrodes;
depositing a passivating layer between about 20 nm and about 500 nm covering a substantial portion of device;
establishing at least one second opening in the passivating layer arranged to correspond to the at least one trench;
the at least one trench comprises a plurality of trenches;
the second electrode is arranged in a "T" or cross configuration (for example) relative to the first electrode so as to separate one or more junctions there between;
the plurality of trenches comprise a first trench and a second trench, where a longitudinal axis of the first trench is at an angle to the longitudinal axis of the second trench, in such embodiments, the angle may be a perpendicular angle;
the width of the second electrode is less than about 500 nm;
the width of the second electrode is less than about 100 nm;
the at least one trench includes a width or diameter of between about 2.5 nm to about 3 nm;
the second electrode is substantially smaller than the first electrode;
the at least one trench is established using reactive ions;
the at least one trench is established using a focused beam of He ions; and
the at least one trench is established using low-energy argon ions.

In some embodiments, a method for manufacturing a device for identifying one or more target molecules is provided which may comprise one or more of (and in some embodiments, several of, and in still some embodiments, all of): depositing a first bottom electrode onto a solid supporting layer, wherein the first electrode including a first area, depositing a dielectric layer over the first electrode, depositing a second top electrode over the dielectric layer, wherein the second electrode includes a second area which is substantially less than the first area, establishing at least one trench through at least the second electrode and the dielectric layer, such that the bottom of the trench exposes a tunnel junction between the first and second electrodes, substantially covering the device with a first passivating layer, and establishing an opening in the passivating layer adjacent the at least one trench.

Some embodiments may comprise, and/or otherwise include (e.g., with respect to the above noted embodiments, or other embodiments disclosed herein) one and/or another of the following features and/or steps:
- the opening in a first passivating layer comprises ion-etching using a mask, where the mask covers comprise at least one of Ta and Ni, in a layer of between about 10 nm and about 500 nm, provided over the first passivating layer;
- depositing a second passivating layer over the mask;
- exposing an opening in the second passivating layer is accomplished, for example, via optical lithography to expose the mask;
- etching the mask to remove an area of the mask corresponding to the opening in the second passivating layer;
- etching is accomplished, for example, using at least one of a nitric, acetic, and sulfuric acid, and/or a ferric chloride solution;
- the first passivating layer is removed, for example, using an argon plasma or a solvent; and
- exposing the assembly to chlorine ions to etch the second electrode to expose the dielectric layer, and thereafter, etching the dielectric layer by exposing the dielectric layer to boron trichloride ions.

In some embodiments, a device for detecting one or more target molecules is provided and may comprise a first bottom electrode having a first thickness, the first electrode deposited on onto a solid supporting layer, a dielectric layer substantially covering the first electrode, a second top electrode having a second thickness, the second electrode being separated from the first electrode by the dielectric layer, where the surface area of the second electrode is less than the surface area of the first electrode, at least one trench is cut, etched or otherwise created through at least the second electrode and dielectric layer such that at least the bottom of the opening exposes the first electrode. In some embodiments, the trench is configured to expose a tunnel junction between the electrodes to facilitate communication of one or more target molecules with the first and second electrodes.

Some embodiments may comprise, and/or otherwise include (e.g., with respect to the above noted embodiments, or other embodiments disclosed herein) one and/or another of the following features:
- the second electrode being substantially smaller than the first electrode;
- the width of the second electrode is less than about 500 nm;
- the width of the second electrode is less than about 100 nm;
- the second electrode comprises a wire, where the wire may include a width of between about 5 nm and about 500 nm, a width of between about 10 nm and about 100 nm, or a width of between about 40 nm and about 80 nm;
- the second electrode may be arranged in a cross or "T" configuration relative to the first electrode so as to separate one or more junctions therebetween;
- at least one adhesion layer arranged beneath at least one of the first and second electrodes;
- the adhesion layer comprises titanium;
- the adhesion layer includes a thickness of about 0.01 nm to about 1 nm, or a thickness of about 0.5 nm;
- the dielectric layer covers substantially all of the first electrode save for a contact area for the first electrode, the contact area configured for connection to a contact pad at the edge of the device;
- $Al_2O_3$ is deposited on the contact area, where the $Al_2O_3$ is deposited in a thickness of between about 1 nm and about 5 nm, or a thickness of about 3 nm;
- first molecules for forming a non-covalent bond with the one or more target molecules, where the electrodes are chemically functionalized with the first molecules;
- at least one of the electrodes is comprised of at least one of palladium, gold and platinum;
- a passivating layer between about 20 nm and about 500 nm covering a substantial portion of the surface of the electrodes; in such embodiments, an electrolyte may also be included, where the passivating layer is configured to separate the electrolyte from the surface area of the electrodes;
- a passivating layer substantially encapsulating the device, the layer being between about 20 nm and about 500 nm in thickness;
- in embodiments with a passivating layer, the passivating layer includes at least one opening arranged to correspond to the at least one trench;
- in embodiments with a passivating layer, the passivating layer comprises PMMA;
- in embodiments with at least one opening in the passivating layer, the at least one opening includes a width between about 4 µm and about 16 µm, and a length of between about 14 µm and about 56 µm;
- in embodiments which include a trench, the trench includes a length, a width and a depth, where the depth of the trench is between about 10 nm to about 500 nm, or between about 30 nm to about 100 nm;
- in embodiments with a trench, the width of the trench is between about 1 µm and about 10 µm, and wherein the length of the trench is between about 1 µm and about 5 µm, or the width of the trench is about 4 µm and wherein the length of the trench is about 2 µm;
- in embodiments with a trench, the trench includes a substantially rectangular shape;
- in embodiments with a trench, a length of the trench is greater than a width of the trench;
- in embodiments with a trench, the at least one trench may comprise a plurality of trenches, and in such embodiments, the plurality of trenches include a length and a width with the length being greater than the width;
- in embodiments with a plurality of trenches, the plurality of trenches are each configured with a rectangular shape;
- in embodiments with a plurality of trenches, the plurality of trenches comprise a first trench and a second trench, where a longitudinal axis of the first trench is at an angle to the longitudinal axis of the second trench, and such angle may comprise a perpendicular angle; and in embodiments with at least one trench, the at least one trench includes a width or diameter of between about 2.5 nm to about 3 nm.

In some embodiments, a method for identifying one or more target molecules is provided, and may comprise one or more of (and in some embodiments, several of, and in some embodiments, all of) the following steps: providing a device according to any of the disclosed embodiments, functionalizing at least a portion of at least one of the electrodes with first molecules, the first molecules configured for forming non-covalent bonds with one or more target molecules, flowing a solution containing one or more target molecules past the electrodes, and detecting the one or more target molecules upon the one or more target molecules forming a non-covalent bond with the first molecules.

BRIEF DESCRIPTION OF THE FIGURES

FIGS. 2A-2D illustrate scanning electron microscope (SEM) images of a device layout prior to channels or trenches (these terms being used interchangeably throughout) being made according to some embodiments of the present disclosure:
    FIG. 2A scale bar corresponding to 500 microns;
    FIG. 2B scale bar corresponding to 100 microns;
    FIG. 2C scale bar corresponding to 50 microns; and
    FIG. 2D scale bar corresponding to 20 microns.

DESCRIPTION OF THE EMBODIMENTS

Figure 1A:
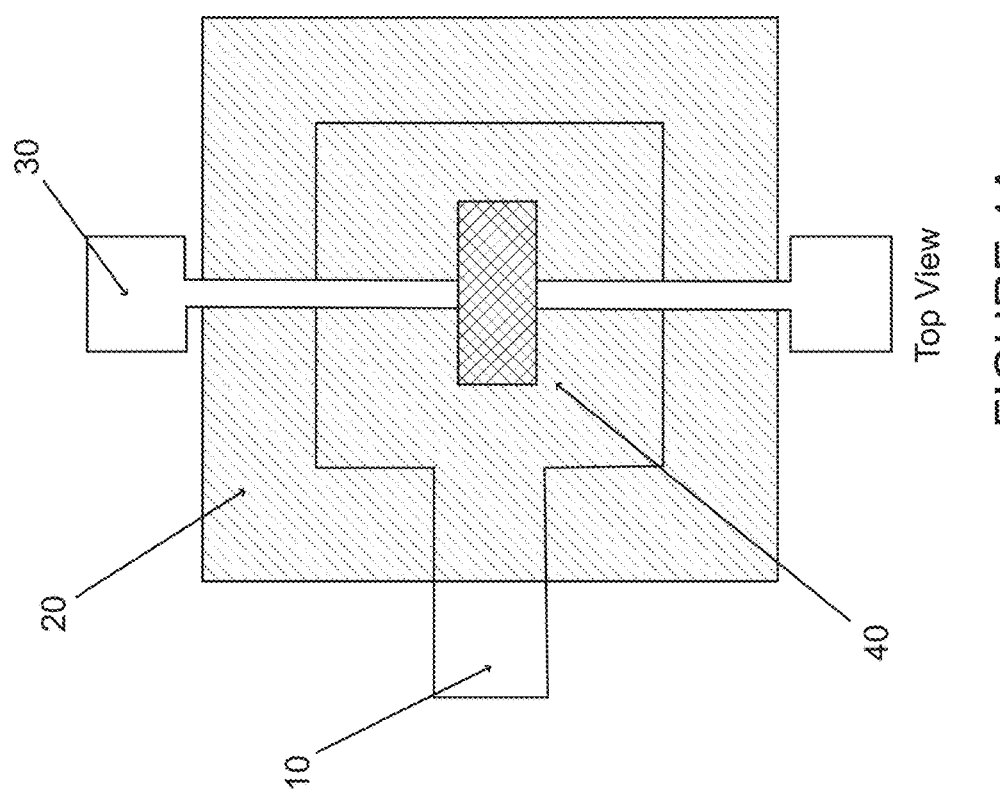
FIGS. 1A-1B illustrates a plan view (FIG. 1A) and a cross section (FIG. 1B) of a device according to some of the embodiments of the present disclosure.
Figure 1B:
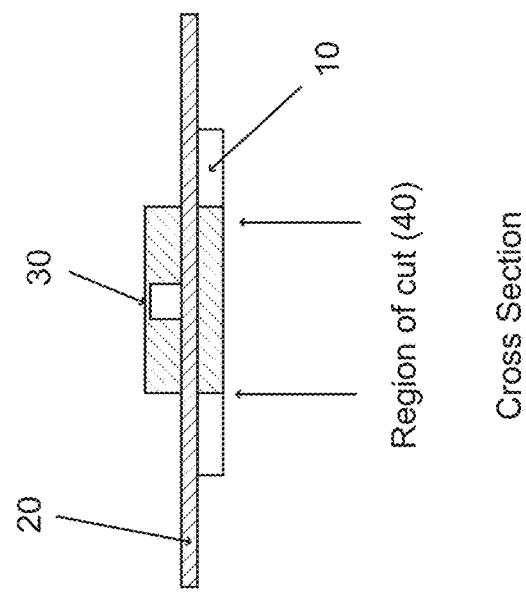

FIGS. 1A and 1B illustrate an arrangement of a device for sensing target molecules according to some of the embodiments of the present disclosure. As shown, a designated area (typically about 50 microns by about 50 microns or greater) of electrode (10) is deposited onto a solid supporting layer, including, for example, hafnium oxide, a polymer membrane, an oxidized silicon wafer, and/or a silicon nitride layer (for example) atop a silicon wafer (or other supporting layer). In some embodiments, about 9 nm of Pd on top of about 0.5 nm Ti adhesion layer, but according to some embodiments, other noble metals such as Pt and Au may be used. In some embodiments, a dielectric layer (20) may be deposited over the bottom electrode, substantially covering it (for some embodiments, covering the bottom of the electrode entirely). However, in some embodiments, an area is left uncovered for connection to a contact pad at the edge of the device. This contact area may be, for example, a 1 to 5 nm (with 2 nm preferred in some embodiments) layer of $Al_2O_3$ fabricated using atomic layer deposition (for example).

In some embodiments, a top electrode (30) may then be deposited over the dielectric layer. In some embodiments, this may also be about a 9 nm evaporated layer of Pd on top of about a 0.5 nm Ti adhesion layer. The second electrode may be made much smaller, relatively, than the lower, first electrode, for example, a wire of between about 10 and about 100 nm in width (in some embodiments, this may be a wire of about 40 to about 80 nm). In some embodiments, such dimensions allows minimization of background, direct tunneling through the dielectric, and may also minimize the probability of encountering a pinhole in the dielectric.

In some embodiments, in order to gain access to a tunnel junction between the electrodes for target molecules (e.g., analyte) in solution, a trench (40) may be cut through portions of the device (and in some embodiments, the entire device). Such a trench may be made with a focused ion beam, or FIB, (for example), though reactive ion etching may also be used. In some embodiments, the depth of the trench may be between about 30 to about 100 nm. An advantage of some of such embodiments is that the trench need only intersect the top wire and dielectric, exposing the bottom electrode at some point for a junction to be made/accessible. Thus, according to such embodiments, critical alignment may not be required.

Figures 2A, 2B:
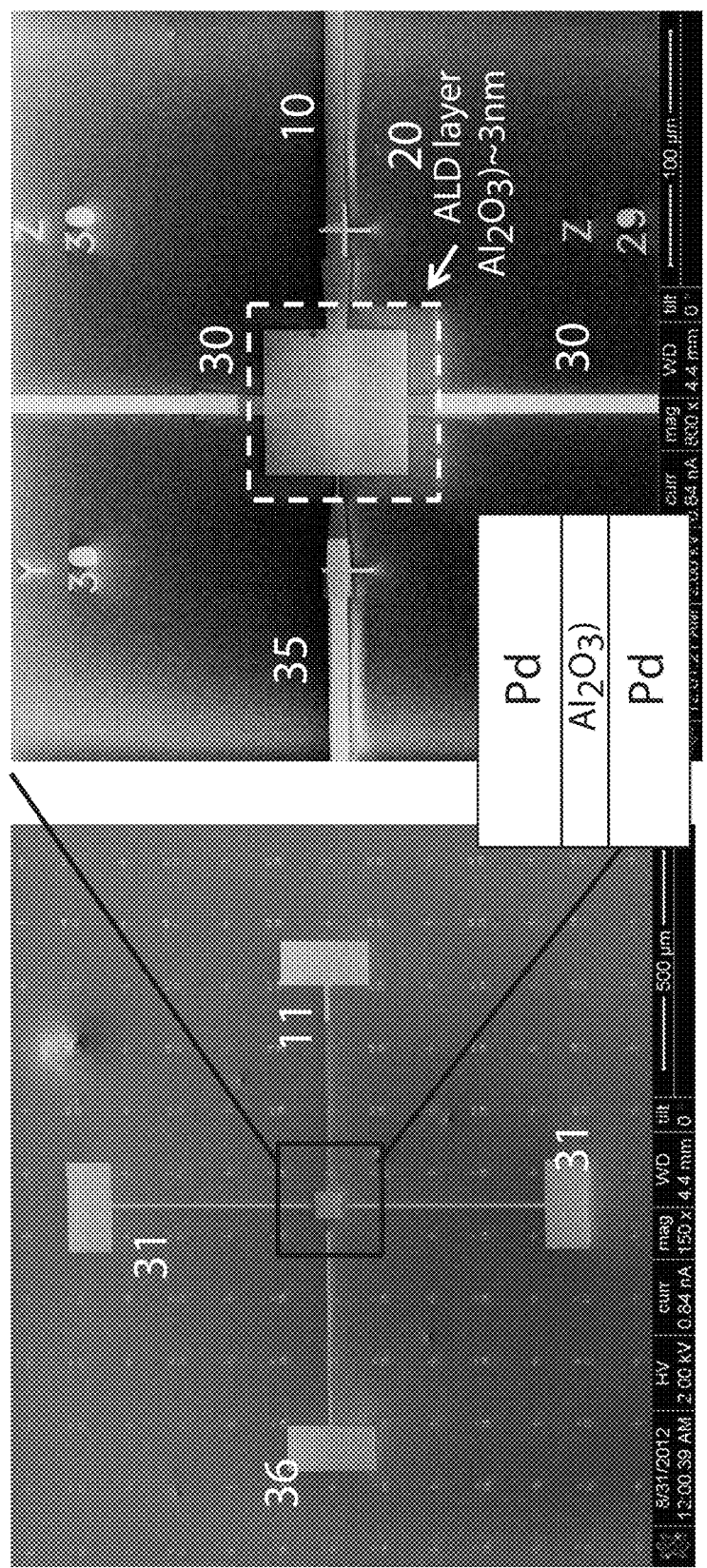

FIG. 2A shows an SEM image of a device according to some embodiments of the present disclosure. Here, the top electrode has been arranged in a "t" formation to allow for separate tunnel junctions (e.g., three) to be made on each device (a simple line electrode is shown in FIG. 1 for clarity). Each electrode runs to a respective pad (e.g., 31, 36 in FIG. 2 connect to the narrow top electrodes, 11 connects to the large bottom electrode). FIG. 2B shows an area where $Al_2O_3$ is deposited (by the dashed box) according to some embodiments. The third wire (forming the t) is labeled 35. FIG. 2C shows the device at increased magnification so that the top "t" is visible. FIG. 2D shows the top electrode at yet higher magnification, according to some embodiments.

Figure 3:
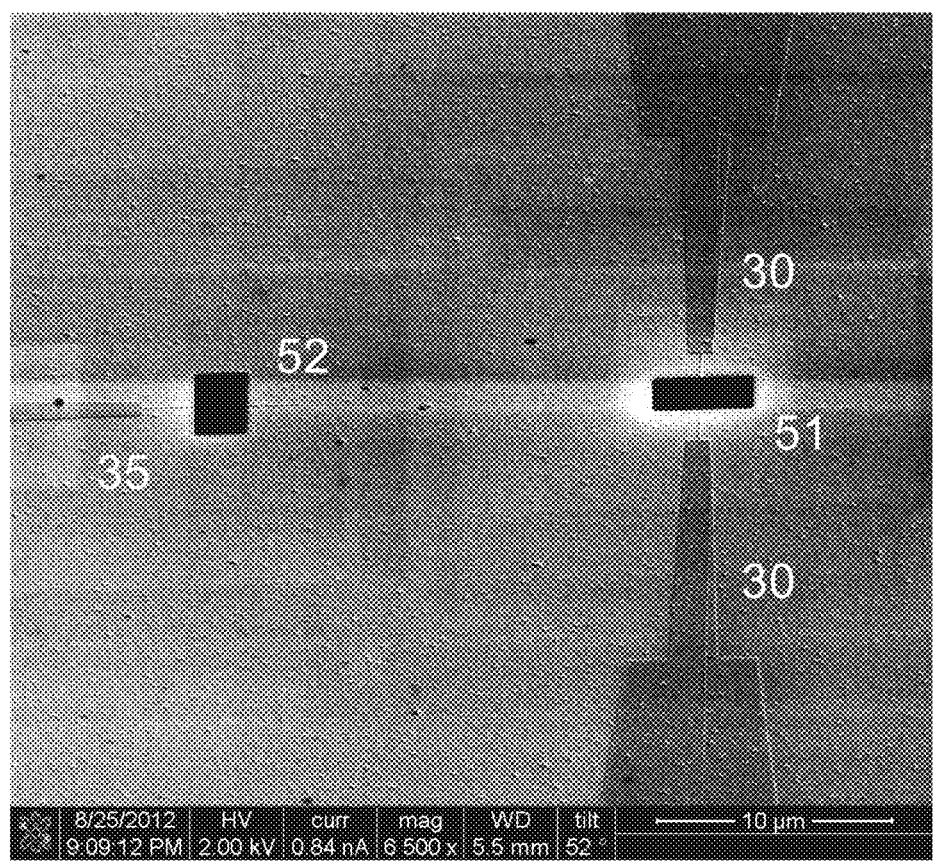
FIG. 3 illustrates a tilted SEM image (scale bar corresponding to 10 microns) after cutting of channels in a device according to some embodiments of the present disclosure.

FIG. 3 shows an SEM image of a device after drilling of trenches (52 and 51) by FIB according to some embodiments. For example, each trench is about 4 microns wide in a dimension perpendicular to the wire and about 2 microns long in the dimension parallel to the wire length (these dimensions are distorted by the tilting required to form an image in the FIB). Trench 52 is about 40 nm in depth and trench 51 is about 80 nm in depth. These dimensions are for example purposes only, as such trenches may be larger or smaller (and may be significantly larger or smaller), as well as shallower or deeper, so long as the top and bottom electrodes are exposed (according to some embodiments).

Figure 4A:
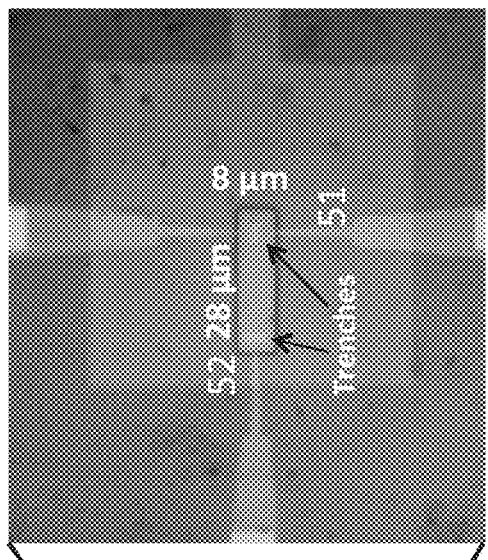
FIGS. 4A and 4B are optical images of a device according to some embodiments of the present disclosure, illustrating a fluid well in a passivating (e.g., PMMA) overlayer (trenches are visible in FIG. 4B).
Figure 4B:
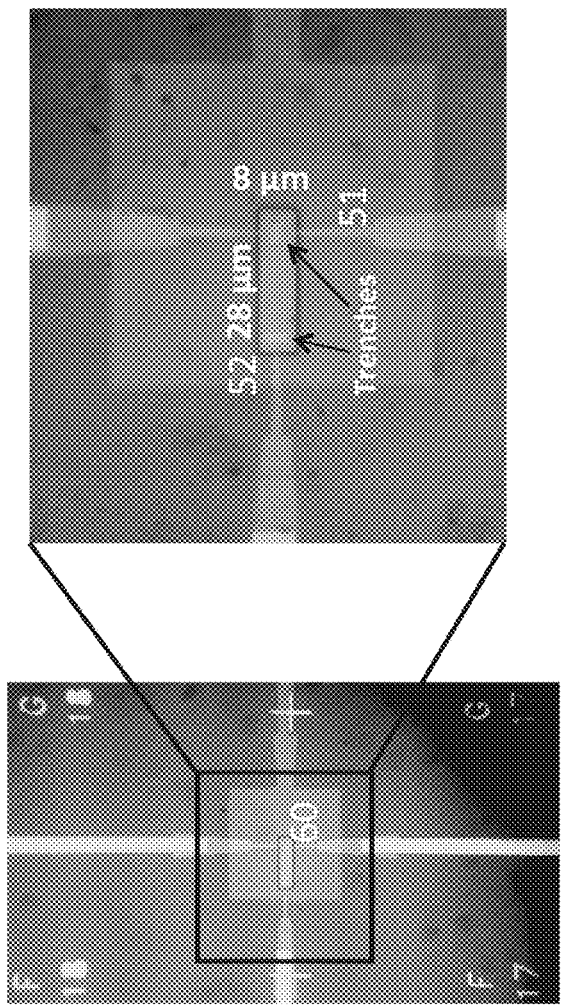
Figure 4C:
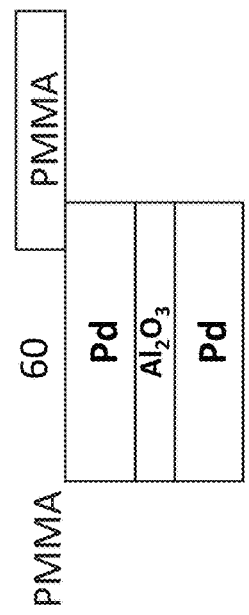
FIG. 4C is a schematic cross-section showing the formation of the well by removal of PMMA in the area enclosed by the black box outline in FIG. 4A.

FIG. 4 illustrates exemplary embodiments of a device configured for fluid measurements. In such embodiments, a passivating layer of Poly(methyl methacrylate), or PMMA, is formed over substantially the entire device (for example). The layer may be between about 20 nm and about 500 nm in thickness, though in some embodiments, the layer is about 100 nm. Openings or windows (such terms used interchangeably throughout) may then be made lithographically (for example) for the external contacts. A small opening (60) may be made over the two trenches. In some embodiments, the opening may be about 8 microns by about 28 microns (note, in some embodiments, only a few square microns of electrode exposed to the electrolyte provides necessary functionality). FIG. 4C illustrates a cross section through the device with the well in place (according to some embodiments).

Figure 5:
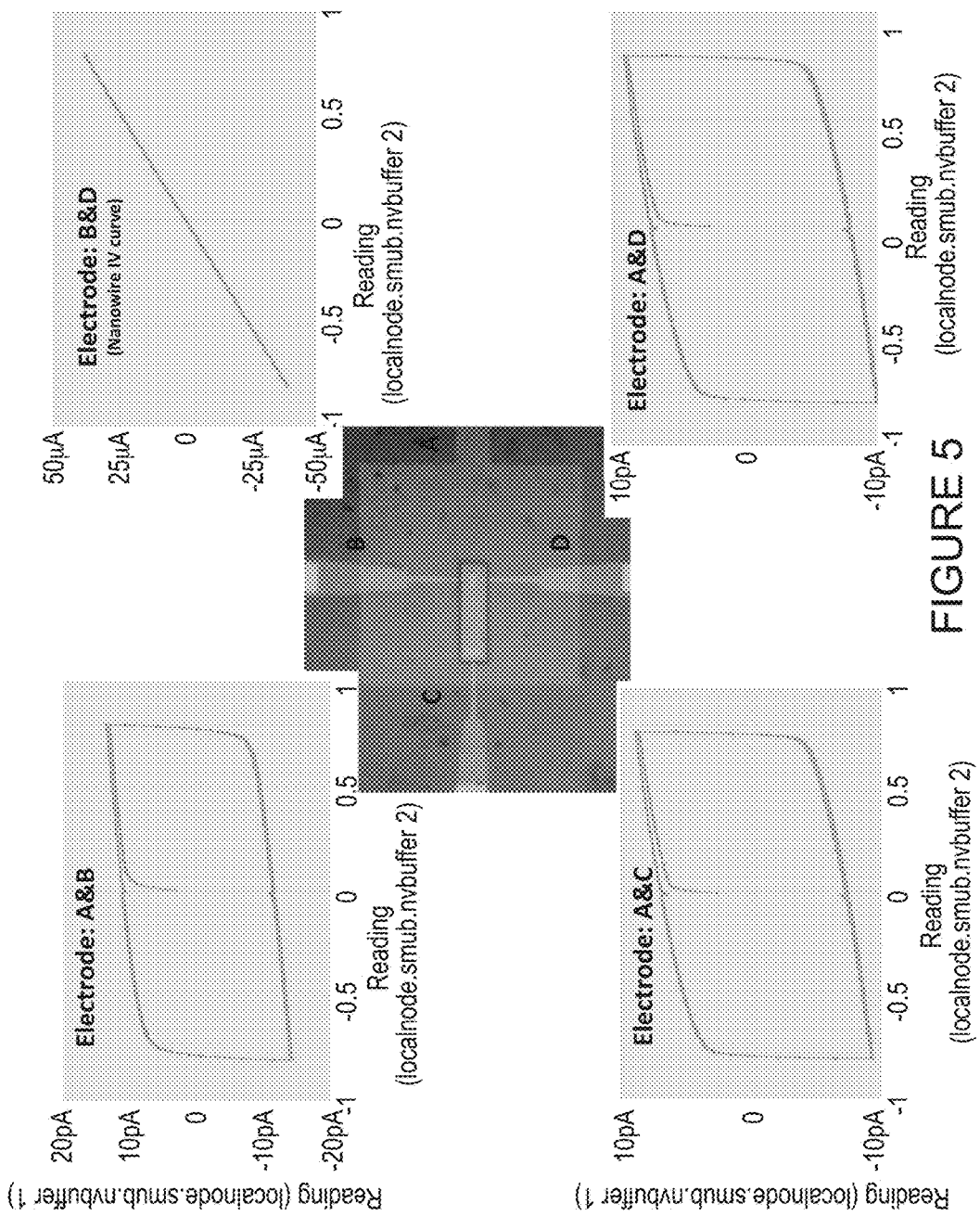
FIG. 5 illustrates a graph of tunneling current vs. voltage, sweeping from −0.8V to +0.8V, for various electrode arrangements, gathered from a device according to some embodiments of the present disclosure.

In some embodiments, tunnel currents through the dielectric layer may be notably small when 80 micron wide wires are utilized (for example, several picoamps at 0.8V). FIG. 5 illustrates current vs. voltage plots for the three junctions on a chip after trenches are cut, according to some embodiments, and also correspond to several picoamps at 0.8V. In contrast, the current through a wire (electrodes B and D) before cutting of trenches may provide a signal that the wire is continuous. It is worth noting that hysteresis of about 20 pA is an artifact of the data collection system. The actual tunnel current is about 5 pA at 0.8V (between top and bottom electrodes, AB, AC and AD with the electrode labels as shown in the image in the center). The current between B and D shows the continuity of this wire prior to cutting of the trench.

Figure 6:
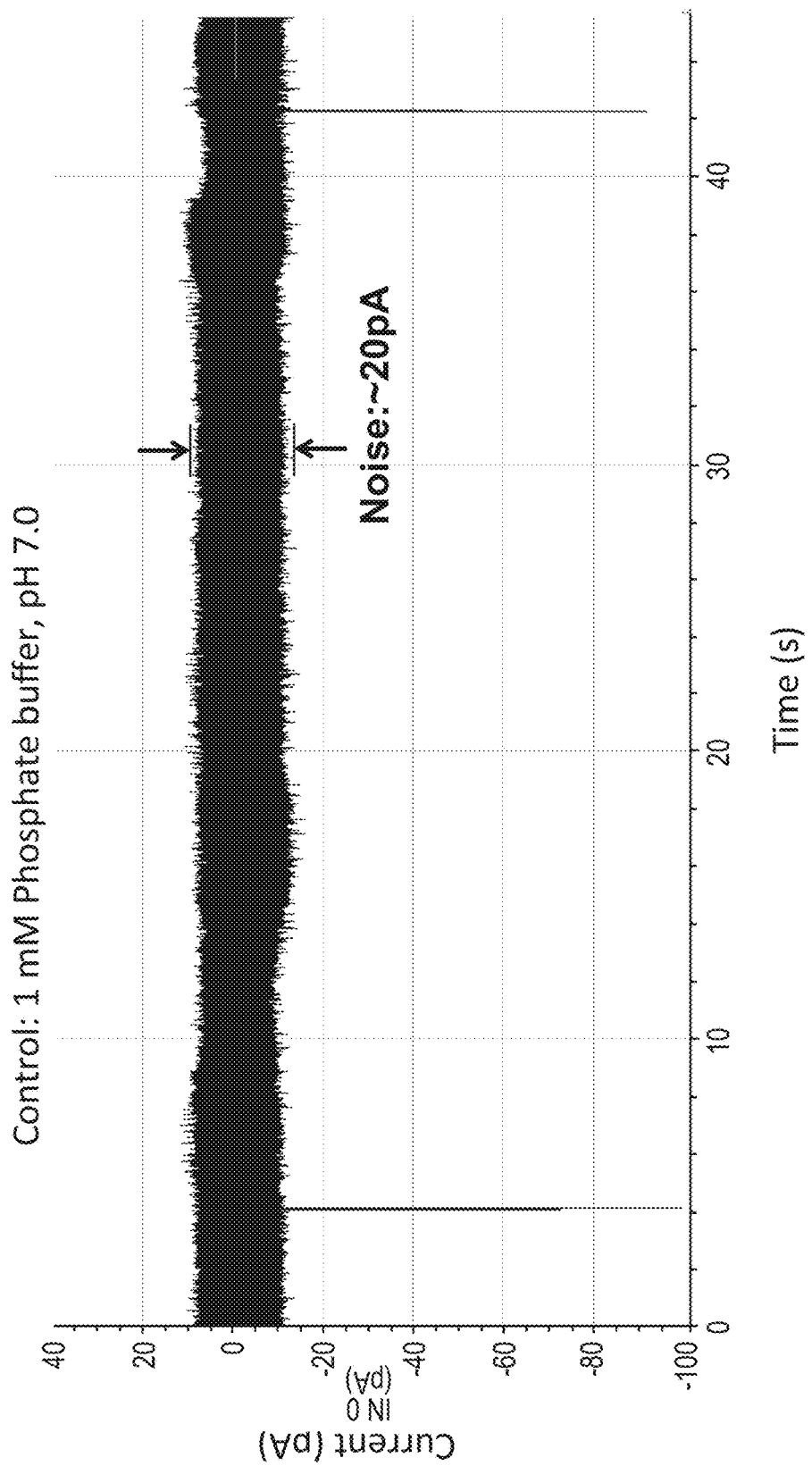
FIG. 6 illustrates a graph of current vs. time over a 45 second time period of control signals for a device according to some embodiment of the present disclosure.

In some embodiments, the electrodes may be functionalized with 4(5)-(2-mercaptoethyl)-1H imideazole-2-carboxamide. This may be accomplished, according to some embodiments, by soaking the devices in a 0.5 mM solution of the molecule in ethanol for 24 h (for example). After treatment, tests on devices with a 1 mM phosphate buffer solution (pH=7.0) yield the current vs. time graph illustrated in FIG. 6. Using a faster amplifier, so that more noise is evident (20 pA peak to peak), results in features which can be recorded on a ms timescale. For this example, the bias is 0.4V and the average background current is less than 5 pA.

Figure 7:
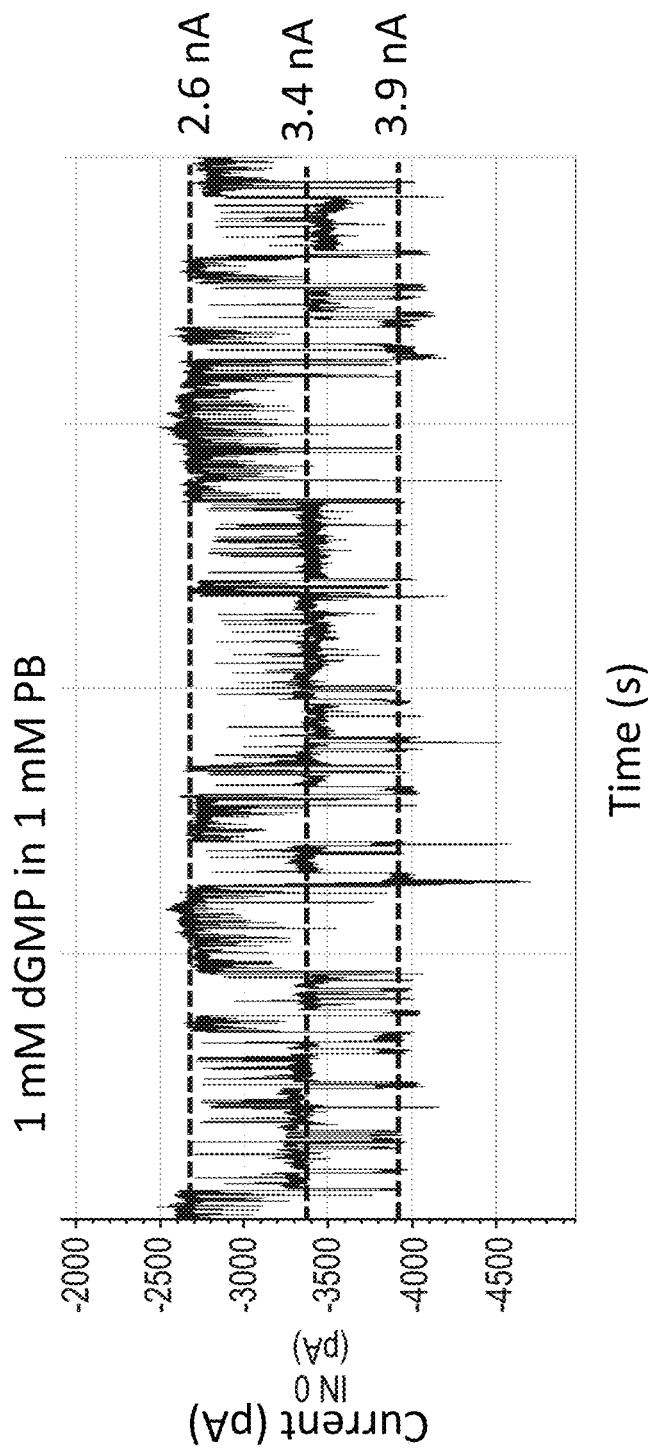
FIG. 7 is a graph of current produced in a device according to the present disclosure vs. time, after introduction of a 1 mM solution of dGMP in a 1 mM phosphate buffer.

In some embodiments, when a 1 mM solution of deoxyguanosine monophosphate (in 1 mM phosphate buffer) is placed in the well, the background current increases in a substantial manner (to 2.6 nA). Superimposed on this current may be three-level switching behavior (to 3.4 and 3.9 nA) characteristic of signals from just one or two molecules as illustrated in FIG. 7. In FIG. 7, current scale is pA and lines provide three levels of signal (in nA); no signals are seen when the electrodes lack the imideazole-2-carboxamide functionalization. When the junction is rinsed with clean phosphate buffer (i.e., no analyte), the current returns to just a few pA (with no evidence of the telegraph noise). Thus, in some embodiments, the signal may be generated by the target molecule/analyte and single molecules may be detected. In another control experiment, 1 mM dGMP was added to a device that lacked the imideazole-2-carboxamide reader molecules, and no spikes were observed. After functionalizing the device with imideazole-2-carboxamide, signals corresponding to those in FIG. 7 were observed. Thus, according to some embodiments, the functionalization of the reading electrodes enables recordation of single molecule signals with such a large (2.5 to 3 nm) tunnel gap.

Figure 8:
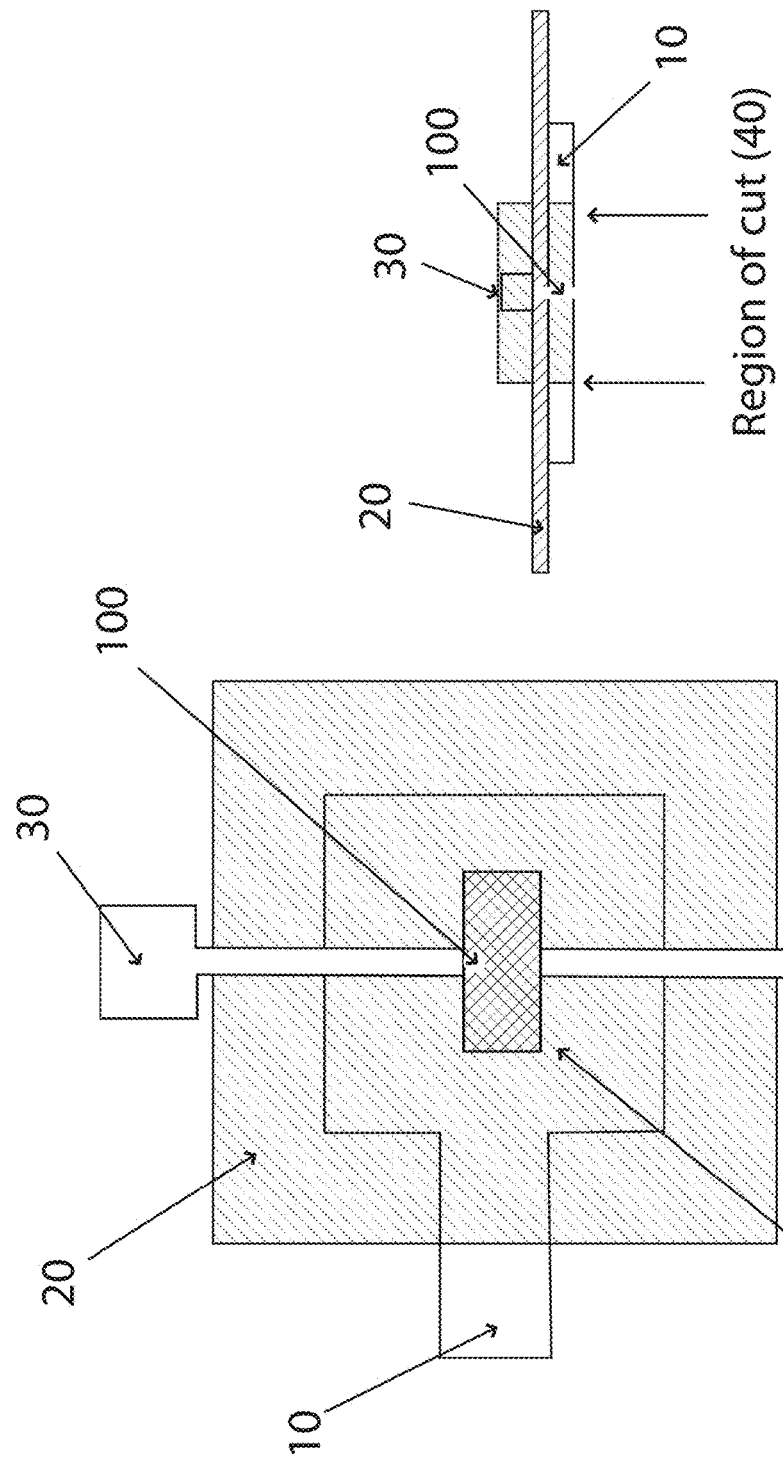
FIGS. 8A-8B illustrate a plan view (FIG. 8A) and a cross section (8B) of a device according to some of the embodiments of the present disclosure, illustrating a manner in which a nanopore can be added adjacent a tunnel gap.

In order to make sequential reads of the composition of a polymer, such as (for example) the base sequence of DNA or an amino acid sequence of a protein (or the sugar sequence of a polysaccharide), the molecule may be passed through a nano sized opening (nanopore) adjacent to the electrodes. An exemplary configuration for accomplishing this is shown in FIG. 8. In some embodiments, and in this case illustrated in FIG. 8, the depth of the trench (40) may be made about equal to the sum of one or both electrode thicknesses plus the thickness of the dielectric (for example), which eliminates the need to drill a pore through the electrode material. Thus, a nanopore (100) may be drilled immediately adjacent to the edge of one of the electrode pairs, through the underlying substrate by means of, for example, a focused electron beam as is well known in the art. According to such embodiments, one alignment step may be all that is required for a device (the drilling of the nanopore may be carried out using a transmission electron microscope, TEM or scanning transmission electron microscope, STEM, and the like) and damage to the electrodes may be avoided.

In some embodiments, the cutting of an electrode gap using a Ga beam FIB may include a disadvantage in that considerable energy is transferred into the tunnel junction by the heavy Ga ions, which may cause damage to one and/or another of the metal electrodes. Furthermore, implantation of Ga ions in the region of the junction, in some instances, may lead to unpredictable electrical characteristics for the device. For these reasons, devices based on cuts with a Ga FIB may provide low yields. To that end, in some embodiments, the dielectric layer (e.g., $Al_2O_3$) may be made thicker than required such that damaged devices in which the electrodes are brought closer together can operate. In some instances, a consequence of this may be that the signals (see FIG. 7), while characteristic of the analyte, are difficult to understand since the junction geometry may not be well controlled.

Figure 9:
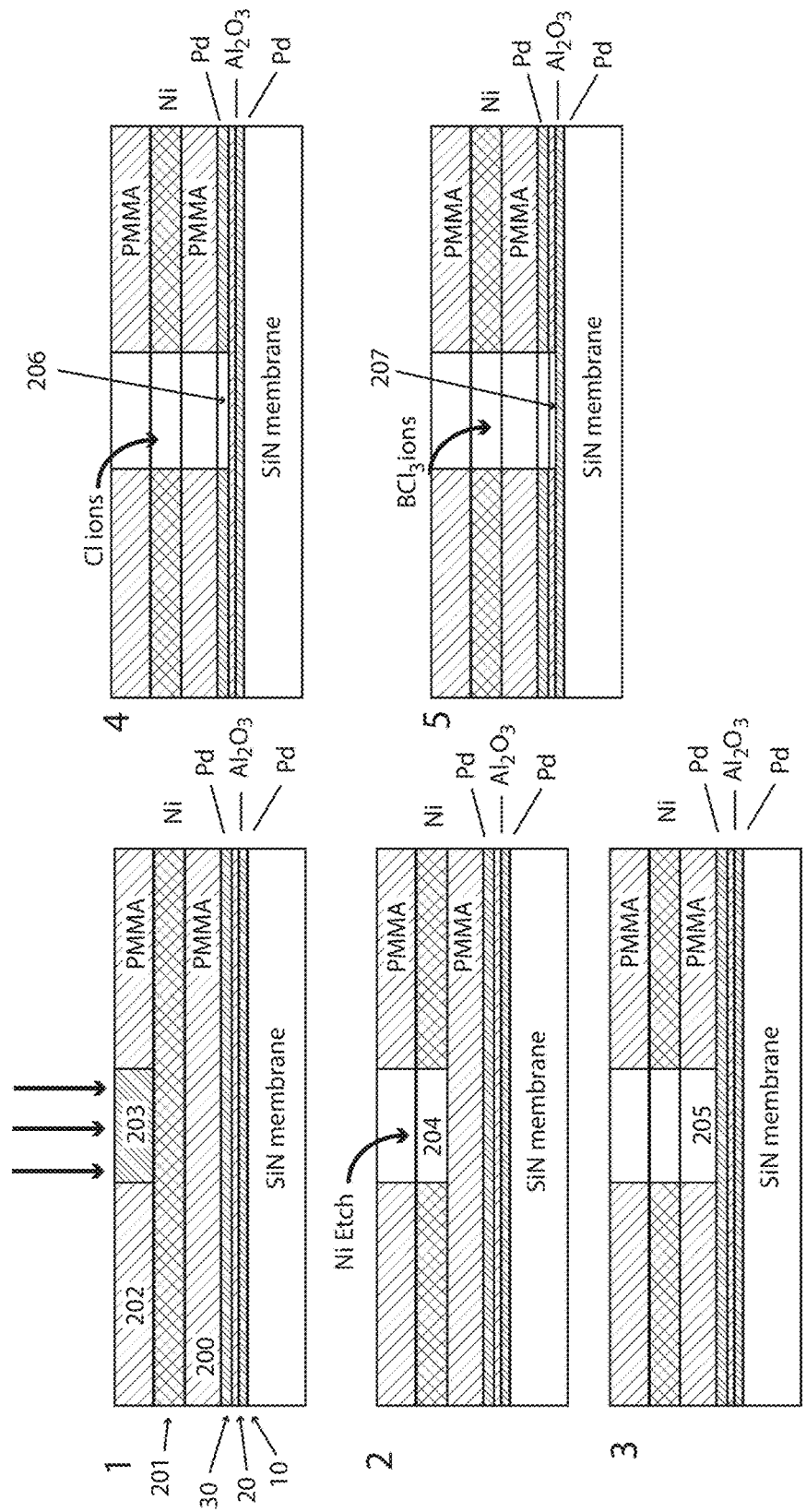
FIG. 9 illustrates processing steps (steps 1-5) to cut an opening into the tunnel junction using reactive ion etching, according to some embodiments of the present disclosure.

FIG. 9 illustrates a device according to some embodiments of the present disclosure, where the electrode arrangement may be cut into (e.g., to establish one or more trenches) using a technique of reactive ion etching, for example. Referring to panel 1 of FIG. 9, the electrode/dielectric arrangement/stack (10, 20, 30) may be covered with a protective layer of PMMA, of a thickness of about 100 nm to about 1000 nm (200). A mask that resists the ions used to etch the junction materials may be formed on top of this PMMA layer, and may be of Ta or Ni, for example. In some embodiments, a layer of about 10 nm to about 500 nm of Ni (201) is deposited on top of the PMMA layer using, for example, e-beam evaporation. In some embodiments, a focused ion beam can be used to make an opening into the Ni or Ta window, stopping before the Ga beam damages the tunnel junction.

In some embodiments, the Ni (or Ta) layer may be covered with PMMA (202) and optical lithography may be used to expose an opening or window in the PMMA (203), as shown in panel 1 of FIG. 9 for a positive resist, though a negative resist can be used with the appropriate mask. After opening of the PMMA opening/window, a nickel etch may then be used to remove the nickel film in the desired region (204). This etch can be, for example, a nitric/acetic/sulfuric acid mix or a ferric chloride solution. The underlying PMMA may then be removed (see, 205 in panel 3, FIG. 9) using, for example, an argon plasma or a short exposure to solvent, thereby exposing the tunnel junction structure (10, 20, 30) below.

In some embodiments, the assembly may then be placed in a reactive ion etcher (RIE). For example, it may be first exposed to chlorine ions which etch the top palladium electrode (see (206) of Panel 4 of FIG. 9). The assembly may then be exposed to boron trichloride ions which can be used to etch the $Al_2O_3$ dielectric layer (see (207) of Panel 5 of FIG. 9).

Figure 10:
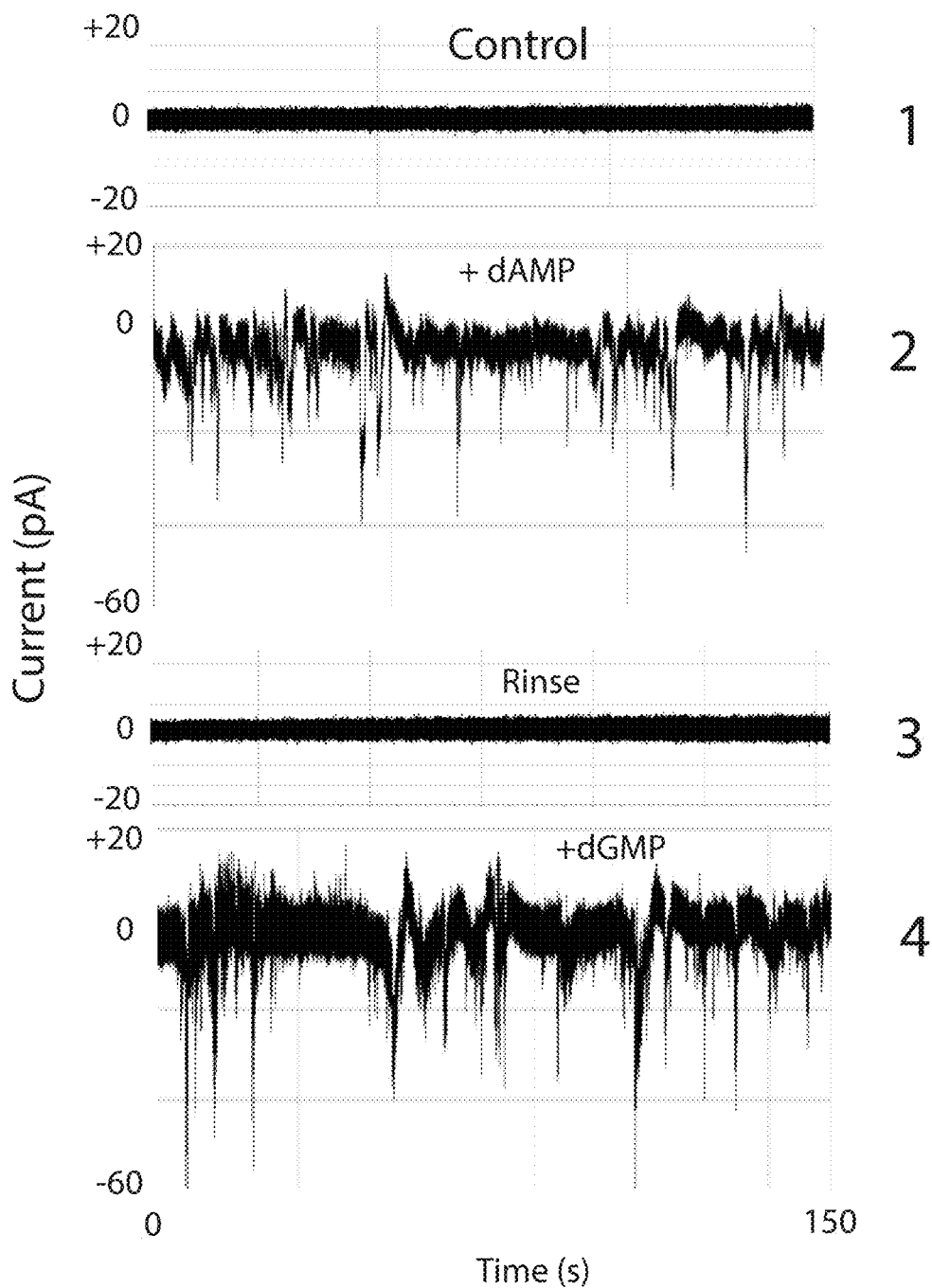
FIG. 10 is a graph of chemical recognition signals obtained from a device according to some embodiments of the present disclosure, having a 2 nm $Al_2O_3$ dielectric layer cut using a reactive ion etching process.

Using this technique, cuts may be made reliably into devices with, for example, a 2 nm (or thereabout) $Al_2O_3$ layer, which corresponds to significant improvement on etching using the Ga FIB where the starting thickness of the dielectric may be required to be thicker than 2 nm (e.g., between about 3 to about 5 nm). FIG. 10 is a graph illustrating typical signals obtained from such a device (according to some embodiments) in which the junction is cut using reactive ion etching. In some embodiments, in the absence of an analyte, or in the presence of analyte, but absence of chemical functionalization of the electrodes, the tunneling signal with electrolyte in the tunnel junction remains near 0 pA ("control" in panel 1 of FIG. 10). When adenosinemonophosphate ("dAMP") is added to the electrolyte solution, current peaks are observed (panel 2). The current returns again to near zero when the junction is rinsed with clean electrolyte (panel 3). When guanosinemonophosphate ("dGMP") is added (panel 4), current peaks return. One of skill in the art will note that the magnitude of the current peaks is bigger for dGMP than for dAMP, evidencing chemical discrimination. These signals are different from those generated by the Ga FIB cut junctions (FIG. 7). Such signals are much more like signals produced by a STM, giving evidence that the junction produced by reactive ion etching may be simpler than the junction produced by Ga FIB milling.

Figure 11:
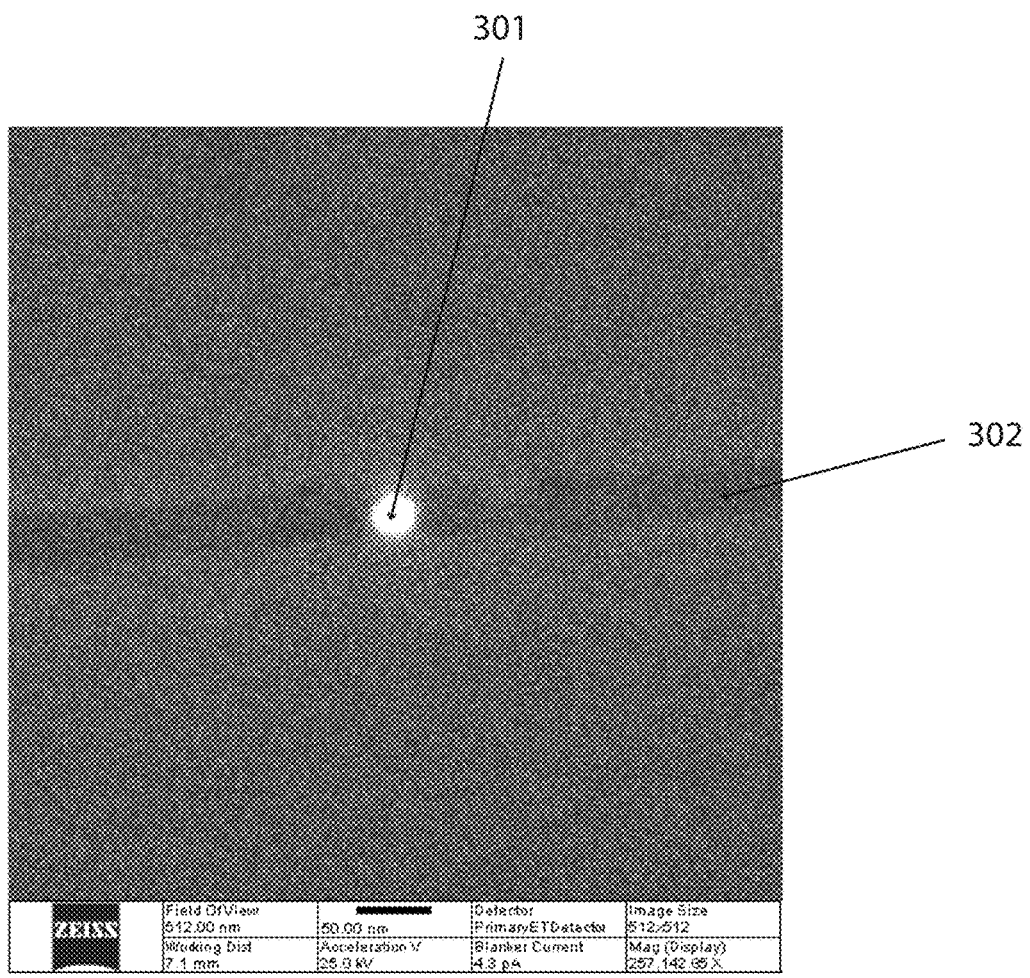
FIG. 11 illustrates a device with an opening according to some embodiments, the opening being fabricated using a focused He ion beam.

In some embodiments, a possible disadvantage of RIE may be that the size of the cut through the junction may be limited by the lithography used to cut the Ni or Ta mask. An alternative to Ga ion FIB is to use He ion FIB. The He ion FIB generally does not cause the electronic modifications produced by Ga ions (when they implant into the sample). He ions also deposit less energy into the target (because of their smaller mass) and are thus less destructive. FIG. 11 shows an opening/nanopore (301) of about 20 nm diameter (the scale bar corresponds to 50 nm) drilled into a device (302) on a 50 nm thick silicon nitride membrane. This device was made with 10 s exposure to a tightly focused 25 keV beam of He ions. Similar devices, according to some embodiments, have been successfully drilled and produced signals characteristic of analytes placed into the junction.

In some embodiments, low-energy (e.g., 60 eV) argon ions may be used. The speed of etching using the low-energy argon ions is such that a hard mask is not needed. To protect the tunnel junctions from the ions, a PMMA resist of about 600 to about 800 nm thickness may be used. For example, a Kauffman gridded ion source was operated at a beam current of 15 to 20 mA with an accelerating voltage of 60V. Molecule detection devices according to some embodiments which were exposed to the beam for times that varied between about 5 and 15 minutes produced chemical tunnel signals corresponding to those shown in FIG. 10.

Any and all references to publications or other documents, including but not limited to, patents, patent applications, articles, webpages, books, etc., presented in the present application, are herein incorporated by reference in their entirety.

Example embodiments of devices, systems, and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices, which may further include any and all elements from any other disclosed methods, systems, and devices. In other words, elements from one and/or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

CITATIONS

1. HUANG, S., J. HE, S. CHANG, P. ZHANG, F. LIANG, S. LI, M. TUCHBAND, A. FUHRMAN, R. ROS, AND S. M. LINDSAY, *IDENTIFYING SINGLE BASES IN A DNA OLIGOMER WITH ELECTRON TUNNELING*. NATURE NANOTECHNOLOGY, 2010. 5: P. 868-73.
2. LINDSAY, S., J. HE, O. SANKEY, P. HAPALA, P. JELINEK, P. ZHANG, S. CHANG, AND S. HUANG, *RECOGNITION TUNNELING*. NANOTECHNOLOGY, 2010. 21: P. 262001-262013.

What is claimed is:

1. A device for detecting one or more target molecules comprising:
    a first electrode having a first thickness;
    a dielectric layer covering the first electrode;
    a second electrode having a second thickness, the second electrode being separated from the first electrode by the dielectric layer, wherein the surface area of the second electrode is less than the surface area of the first electrode; and
    at least one trench cut or etched through at least the second electrode and dielectric layer and configured to expose a junction between the electrodes to facilitate connection of one or more target molecules with the first and second electrodes.

2. The device according to claim 1, wherein the second electrode comprises a wire.

3. The device according to claim 1, further comprising at least one adhesion layer arranged beneath at least one of the first and second electrodes.

4. The device according to claim 1, wherein the dielectric layer covers substantially all of the first electrode save for a contact area for the first electrode, the contact area configured for connection to a contact pad at the edge of the device.

5. The device of claim 1, further comprising first molecules for forming a non-covalent bond with the one or more target molecules, wherein the electrodes are chemically functionalized with the first molecules.

6. The device of claim 1, further comprising a passivating layer between about 20 nm and about 500 nm in thickness covering a substantial portion of the surface of the electrodes.

7. The device of claim 1, further comprising a passivating layer substantially encapsulating the device, the layer being between about 20 nm and about 500 nm in thickness.

8. The device according to claim 1, wherein the at least one trench includes a plurality of trenches.

9. The device of claim 1, wherein the second electrode is arranged in a cross or "T" configuration relative to the first electrode so as to separate one or more junctions therebetween.

10. The device of claim 1, wherein the at least one trench has a width or diameter of between about 2.5 nm to about 3 nm.

11. A device for detecting one or more target molecules comprising:
- a first electrode, the first electrode deposited on a supporting layer;
- a dielectric layer covering the first electrode;
- a second electrode separated from the first electrode by the dielectric layer, wherein the surface area of the second electrode is less than the surface area of the first electrode; and
- at least one trench cut or etched through at least the second electrode and dielectric layer and configured to expose a junction between the electrodes to facilitate connection of one or more target molecules with the first and second electrodes.

* * * * *